United States Patent

Sankaram et al.

Patent Number: 6,132,766
Date of Patent: *Oct. 17, 2000

[54] MULTIVESICULAR LIPOSOMES WITH CONTROLLED RELEASE OF ENCAPSULATED BIOLOGICALLY ACTIVE SUBSTANCES

[75] Inventors: Mantripragada Bhima Sankaram, San Diego; Sinil Kim, Solana Beach, both of Calif.

[73] Assignee: SkyePharma Inc., San Diego, Calif.

[*] Notice: This patent is subject to a terminal disclaimer.

[21] Appl. No.: 09/045,236

[22] Filed: Mar. 20, 1998

Related U.S. Application Data

[62] Division of application No. 08/898,017, Jul. 21, 1997, abandoned, which is a continuation of application No. 08/473,013, Jun. 6, 1995, abandoned, which is a continuation of application No. 08/153,657, Nov. 16, 1993, abandoned.

[51] Int. Cl.$^7$ .................................................... A61K 9/127
[52] U.S. Cl. ................... 424/450; 424/417; 424/DIG. 8; 264/4.1; 264/4.3; 264/4.6
[58] Field of Search ................................ 424/1.21, 9.321, 424/9.51, 417, 450; 264/4.1, 4.3, 4.6; 436/829; 935/54

[56] References Cited

U.S. PATENT DOCUMENTS

| | | |
|---|---|---|
| 4,078,052 | 3/1978 | Papahadjopoulos . |
| 4,089,801 | 5/1978 | Schneider . |
| 4,145,410 | 5/1979 | Sears . |
| 4,224,179 | 9/1980 | Schneider . |
| 4,235,871 | 11/1980 | Papahadjopoulos et al. . |
| 4,310,506 | 1/1982 | Baldeschwieler et al. . |
| 4,394,372 | 7/1983 | Taylor . |
| 4,522,803 | 6/1985 | Lenk et al. . |
| 4,588,578 | 5/1986 | Fountain et al. . |
| 4,599,227 | 7/1986 | Dees et al. . |
| 4,610,868 | 9/1986 | Fountain et al. . |
| 4,752,425 | 7/1988 | Martin et al. . |
| 4,769,250 | 9/1988 | Forssen . |
| 4,771,612 | 1/1988 | Janoff ....................................... 424/1.1 |
| 4,781,871 | 11/1988 | West, III et al. . |
| 4,920,016 | 4/1990 | Allen et al. . |
| 4,975,282 | 12/1990 | Cullis ....................................... 424/450 |
| 5,000,959 | 3/1991 | Iga et al. . |
| 5,021,200 | 6/1991 | Vanlerberghe et al. . |
| 5,077,056 | 12/1991 | Bally et al. . |
| 5,204,112 | 4/1993 | Hope et al. . |
| 5,211,955 | 5/1993 | Legros et al. . |
| 5,334,381 | 8/1994 | Unger et al. ............................... 424/9 |
| 5,334,391 | 8/1994 | Clark et al. ............................. 424/450 |

FOREIGN PATENT DOCUMENTS

| | | |
|---|---|---|
| 0315467 | 10/1989 | European Pat. Off. . |
| 2050287 | 1/1991 | United Kingdom . |

OTHER PUBLICATIONS

"Topology of Multivesicular Liposomes, a Model Biliquid Foam,"*Langmuir*12;4704–4708, 1996, by M.S. Spencer et al.

Crommelin, Internat. J. Pharmaceutics 16 (1983) p.79.

Huang, Biochemistry, 8:334–352, 1969, "Studies on Phosphatidylcholine Vesicles formation and Physical Characteristics."

(List continued on next page.)

*Primary Examiner*—Gollamudi S. Kishore
*Attorney, Agent, or Firm*—Fish & Richardson P.C.

[57] ABSTRACT

A multivesicular liposome composition containing at least one acid other than a hydrohalic acid and at least one biologically active substance, the vesicles having defined size distribution, adjustable average size, internal chamber size and number, provides a controlled release rate of the biologically active substance from the composition. A process for making the composition features addition of a non-hydrohalic acid effective to sustain and control the rate of release of an encapsulated biologically active substance from the vesicles at therapeutic levels in vivo.

35 Claims, 1 Drawing Sheet

|←—0.02 - 0.5 micron—→| |←—0.2 - 5 micron—→| |←— 1 - 100 micron —→|

Unilamellar Vesicle (ULV)     Multilamellar Vesicle (MLV)     Multivesicular Liposome (MVL)

OTHER PUBLICATIONS

Bangham, A.V. Mol. Bio., 13–238–252, 1965, "Diffusion of univalent ions across the lamellae of swollen phospholipids."

Szoka, et al., Ann. Rev. Biophys. Bioeng., 9:465–508, 1980, "Comparative properties and methods of preparation of lipid vesicles (liposomes)."

Shakiba, et al., Investigative ophthalmology and visual Science, 34(10):2903–10, 1993 Sep., "Evaluation of retinal toxicity and liposome encapsulation of the Anti–CMV Drug 2'–nor–cyclic GMP."

Frucht–Perry, et al., Cornea, 11(5):393–7, 1992 Sep., "Fibrin–enmeshed tobramycin liposomes: single application topical therapy of pseudomonas..."

Assil, et al., Investigative Ophthalmology and Visual Science, 32(13):3216–20, 1991 Dec., "Tobramycin liposomes. Single subconjunctival therapy of ...".

Assil, et al., Investigative Ophthalmology and Visual Science, 32(11):2891–7, 1991 Oct., Lipsome suppression of proliferative vitreoretinopathy. Rabbit....

Turski, et al., Magnetic Resonance in Medicine, 7(2):184–96, 1988 Jun., "Magnetic resonance imaging of rabbit brain after intracarotid injection...".

Skuta, et al., American Journal of Ophthalmology, 103(5):714–16, May 15, 1987, "Filtering surgery in owl monkeys treated with the antimetabolite...".

Assil, et al., Archives of Ophthalmology, 105(3):400–3, 1987 Mar., "Multivesicular liposomes. Sustained release of the antimetabolite...".

Barbet, et al., *Biochimica et Biophysica Acta*, 772(3):347–56, May 30, 1984, "Weat acid–induced release of liposome–encapsulated carboxyflourescein".

Kim et al., Biochim. Biophys. Acta, 646:1, 1981, "Preparation of cell–size unilamellar liposomes with high captured volume and defined size...".

Kim, et al., Biochim. Biophys. Acta, 728:339–348, 1983, "Preparation of multivesicular liposomes".

Kim, et al., Biochim. Biophys. Acta, 793:801, 1985, "Preparation of multilamellar vesicles of defined sized–distribution by solvent–spherule...".

Kim, et al., Cancer Treat. Rep., 71:705–711, 1987, "Multivesicular liposomes containing cytarabine entrapped in the presence of ...".

Kim, et al., Cancer Research, 47:3935–3937, 1987, "Multivesicular Liposomes Containing 1–B–D–arabinofuranosyxcytosine for slow–release intrathecal therapy".

Kim, et al., Cancer Treat Rep., 71:447–450, 1987, "Multivesicular liposomes containing cytosine arabinoside for slow–release...".

Kim, et al., Cancer Chemother Pharmacology, 19:307–310, 1987, "Modulation of the peritoneal clearance of liposomal ara–C by blank liposomes".

Roy, et al., Cancer Chemother. Pharm., 28:105–108, 1991, "Multivesicular liposomes containing bleomycin for subcutaneous administration".

Kim, et al., Reg. Cancer Treat., 2:170–173, 1989, "Intratumoral Chemotherapy with multivesicular liposomes containing 1–b–D–arabino...".

Kim, et al., J. Inf. Dis., 162:750–752, 1990, "Multivesicular liposomes for CSF delivery of retroviral agent DDC".

Chamberlain, et al., Archives of Neurol, 50(3):261–264, 1993, "Treatment of leptomeningeal metastasis with intraventricular administration of ...".

Chatelut, et al., Cancer Them. Pharmacol., 32:179–182, 1993 "A slow–release methotrexate formulation for inrathecal chemotherapy".

Russack, et al., Ann. Neurol., 34:108–112, 1993, "Quantitative cerebrospinal fluid cytology in patients receiving intracavitary chemotherapy".

Kim, et al., J. Clin. Oncol., 11:2186–2193, 1993,"Extended cerebrospinal–fluid cytarabine exposure following intrathecal administration of DTC 101".

Kim, Drugs, 46:618–630, 1993, "Liposomes as carriers of cancer chemotherapy: a review".

Kim, Kim, Kim, Cancer Chemother. Pharmacol., 33:187–190, 1993, "Extended–release formulation of morphine for subcutaneous administration".

Ishii, Liposome Technology, 1:111–121, 1993, "Production and size Control of large unilamellar liposomes by emulsification".

Cullis, et al., Phospholipids and Cellular Regulation, 1:65–123, 1985, "Structural properties and functional roles of phospholipids in...".

Bonetti, et al., Cancer Chemotherapy and Pharmacology, In Press, 1993, "An Extended–release formulation of methotrexate for subcutaneous...".

Kim, et al., Cancer Res., 53;1596–1598, 1993, "Prolongation of drug action in CSF by encapsulation into Depofoam".

Figure 1

MULTIVESICULAR LIPOSOMES WITH CONTROLLED RELEASE OF ENCAPSULATED BIOLOGICALLY ACTIVE SUBSTANCES

CROSS REFERENCE TO RELATED APPLICATIONS

This application is a divisional of U.S. patent application Ser. No. 08/898,017, filed Jul. 21, 1997, now abandoned, which is a continuation of U.S. patent application Ser. No. 08/473,013, filed Jun. 6, 1995, now abandoned, which is a continuation-in-part of U.S. patent application Ser. No. 08/153,657, filed Nov. 16, 1993, now abandoned.

BACKGROUND OF THE INVENTION

1. Field of the Invention

The invention relates to compositions of multivesicular liposomes useful as a drug delivery system and processes for their manufacture.

2. Description of Related Art

Optimal treatment with many drugs requires maintenance of a drug level for an extended period of time. For example, optimal anti-cancer treatment with cell cycle-specific antimetabolites requires maintenance of a cytotoxic drug level for a prolonged period of time. The half-life of many drugs after an intravenous (IV), subcutaneous (SC), intraperitoneal (IP), intraarterial (IA), intramuscular (IM), intrathecal (IT), or epidural dose is very short, being in the range of a fraction of an hour to a few hours. Cytarabine is a highly schedule-dependent anti-cancer drug. Because this drug kills cells only when they are making DNA, prolonged exposure at therapeutic concentration of the drug is required for optimal cell kill. To achieve optimal cancer cell kill with a cell cycle phase-specific drug like cytarabine, two major requirements need to be met: irreversible harm to the host; and second, the tumor must be exposed for a sufficient length of time so that all or most of the cancer cells have attempted to synthesize DNA in the presence of cytarabine.

An example of another class of drugs that are schedule-dependent is the class of aminoglycoside antibiotics. For instance, amikacin is an aminoglycoside antibiotic that has clinically significant activity against strains of both gram negative and gram positive bacteria, but has a serum half-life of about two to three hours. Yet in current practice, the drug is normally administered by intravenous or intramuscular routes once or twice a day. The most commonly used clinical dose is 15 mg/Kg/day, which is equivalent to a maximum recommended daily dose of 1 g per day.

For infections such as those confined to a local region of soft tissue or bone, an implantable drug depot with sustained release properties would be advantageous, both to increase local levels of the drug in the affected tissue and to reduce or avoid the systemic toxicity of the free drug.

Thus, new and better methods for sustained release delivery of drugs in the treatment of disease are needed. The present invention meets this need by providing compositions of multivesicular liposomes useful as a sustained release drug delivery system and a process for their manufacture.

Figure 1:
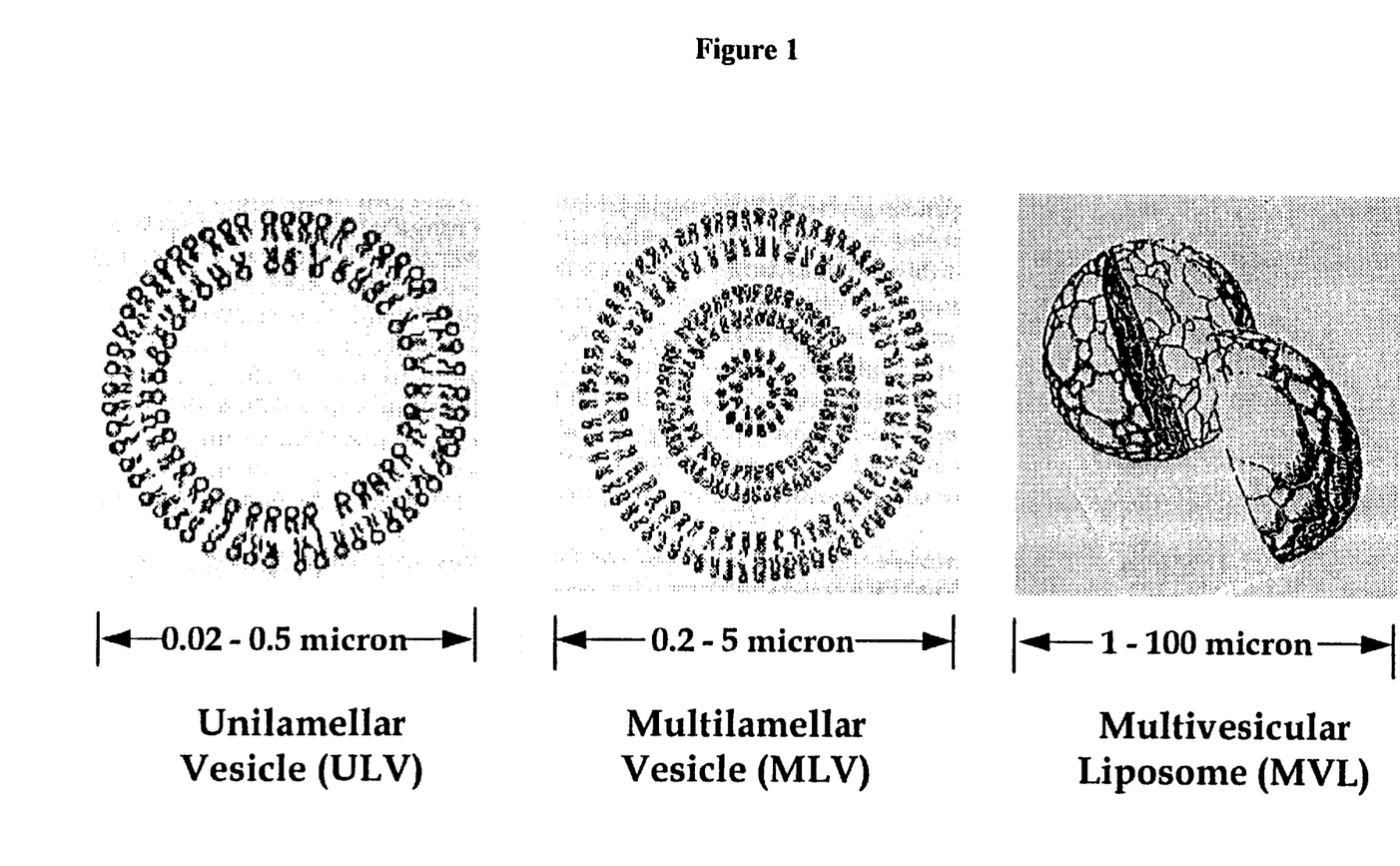
FIG. 1 shows illustrations comparing the internal structures of a unilamellar liposome, a multilamellar liposome, and a multivesicular liposome.

Multivesicular liposomes (MVL), first reported by Kim, et al. (*Biochim, Biophys. Acta,* 728:339–348, 1983), are uniquely different from other lipid-based drug delivery systems such as unilamellar (Huang, *Biochemistry,* 8:334–352, 1969; Kim, et al., *Biochim. Biophys. Acta,* 646:1–10, 1981) and multilamellar (Bangham, et al., *J Mol. Bio.,* 13:238–252, 1965) liposomes. The main structural difference is that in contrast to unilamellar liposomes (also known as unilamellar vesicles, or "ULV"), multivesicular liposomes (MVL) contain multiple aqueous chambers per particle. In contrast to multilamellar liposomes (also known as multilamellar vesicles or "MLV"), the multiple aqueous chambers in multivesicular liposomes are non-concentric. The structural differences between unilamellar, multilamellar, and multivesicular liposomes are illustrated in FIG. 1.

Because of the similarity in acronyms, multivesicular liposomes (MVL) are frequently confused with multilamellar liposomes (MLV). Nevertheless, the two entities are entirely distinct from each other. The structural and functional characteristics of MVL are not directly predictable from current knowledge of ULV and MLV. As described in the book edited by Jean R. Philippot and Francis Schuber (*Liposomes as Tools in Basic Research and Industry,* CRC press, Boca Raton, Fla.,1995, page 19), MVL are bounded by an external bilayer membrane shell, but have a very distinctive internal morphology, which may arise as a result of the special method employed in the manufacture. Topologically, multivesicular liposomes (MVL) are defined as liposomes containing multiple non-concentric chambers within each liposome particle, resembling a "foam-like" matrix; whereas multilamellar vesicles (MLV) contain multiple concentric chambers within each liposome particle, resembling the "layers of an onion".

The presence of internal membranes distributed as a network throughout MVL may serve to confer increased mechanical strength to the vesicle, while still maintaining a high volume:lipid ratio compared with MLV. The multivesicular nature of MVL also indicates that, unlike for ULV, a single breach in the external membrane of a MVL will not result in total release of the internal aqueous contents. Thus, both structurally and functionally the MVL are unusual, novel and distinct from all other types of liposomes. As a result, the functional properties of MVL are not predictable based on the prior art related to conventional liposomes such as ULV and MLV.

The prior art describes a number of techniques for producing ULV and MLV (for example, U.S. Pat. Nos. 4,522,803 to Lenk; 4,310,506 to Baldeschwieler; 4,235,871 to Papahadjopoulos; 4,224,179 to Schneider; 4,078,052 to Papahadjopoulos; 4,394,372 to Taylor; 4,308,166 to Marchetti; 4,485,054 to Mezei; and 4,508,703 to Redziniak). The prior art also describes methods for producing MVL (Kim, et al., *Biochim. Biophys. Acta,* 728:339–348, 1983). For a comprehensive review of various methods of ULV and MLV preparation, refer to Szoka, et al., *Ann. Rev. Biophys. Bioeng.,* 9:465–508, 1980.

In the method of Kim, et al. (*Biochim. Biophys. Acta,* 728:339–348, 1983), the pharmaceutical utility of MVL encapsulating small therapeutic molecules, such as cytosine arabinoside or cytarabine, is limited. Subsequent studies (Kim, et al., *Cancer Treat. Rep.,* 71:705–711, 1987) showed that the release rate of encapsulated molecules into biological fluids can be modulated by encapsulating in the presence of a hydrochloride.

Heretofore, control of the release rate of a biologically active substance from multivesicular liposomes could only be achieved by use of hydrohalides. For a drug-delivery system, it is highly advantageous to be capable of controlling the release rate for encapsulated substances through release rate modifying agents used during manufacture of the liposomes, and to have a wide choice of these release-rate modifying agents.

Accordingly, it is an object of the present invention to provide a controlled release depot preparation of multivesicular liposomes which provides a sustained exposure of a biologically active substance at a therapeutic concentration.

It is a further object of the present invention to provide a method of preparing such depot preparations.

Other and further objects, features, and advantages of the invention are inherent therein and appear throughout the specification and claims.

SUMMARY OF THE INVENTION

The compositions of the present invention comprise multivesicular liposomes (MVL), i.e. lipid vesicles with multiple internal aqueous chambers formed by non-concentric layers, and having internal membranes distributed as a network throughout the MVL, wherein the chambers contain one or more non-hydrohalic acids effective in controlling the release rate of the encapsulated biologically active substance. The present invention also provides methods of making such compositions.

The present multivesicular liposome compositions have high encapsulation efficiency, controlled release rate of the encapsulated substance, well defined, reproducible size distribution, adjustable average size that can be easily increased or decreased, and adjustable internal chamber size and number.

The process for producing these MVL compositions comprises (a) forming an emulsion from a lipid component comprising at least one organic solvent, at least one amphipathic lipid, at least one neutral lipid, and an immiscible first aqueous component comprising at least one biologically active substance and, in the presence of at least one non-hydrohalic acid, (b) mixing the emulsion with a second aqueous component to form solvent spherules, (c) removing the organic solvent from the solvent spherules to form multivesicular liposomes. According to the present invention, addition of one or more non-hydrohalic acids is effective in controlling the release rate of the encapsulated biologically active substance into biological fluids and in vivo.

DESCRIPTION OF THE PREFERRED EMBODIMENTS

The term "multivesicular liposomes" (MVL) as used throughout the specification and claims means man-made, microscopic lipid-vesicles enclosing multiple non-concentric aqueous chambers formed by internal membranes distributed as a network throughout the MVL. In contrast, unilamellar vesicles (ULV) have a single aqueous chamber; and multilamellar liposomes (MLV) have multiple "onion-skin" type of concentric membranes, in between which are concentric aqueous compartments.

The term "solvent spherule" as used throughout the specification and claims means a microscopic spheroid droplet of organic solvent, within which are suspended multiple smaller droplets of aqueous solution.

The term "neutral lipid" means oils or fats that have no membrane-forming capability by themselves and lack a hydrophilic "head" group.

The term "amphipathic lipids" means those molecules that have a hydrophilic "head" group and hydrophobic "tail" group and have membrane-forming capability The term "zwitterionic lipid" means an amphipathic lipid with a net charge of zero at pH 7.4.

The term "anionic lipid" means an amphipathic lipid with a net negative charge at pH 7.4.

The term "cationic lipid" means an amphipathic lipid with a net positive charge at pH 7.4

The term "hydrohalic acid" means hydrofluoric acid, hydrochloric acid, hydrobromic acid, hydroiodic acid, or a combination thereof.

The term "biologically active substance" as used herein means a chemical compound, other than any acid used as a release-rate modifying agent according to the present invention, that is known in the art as having utility for modulating biological processes so as to achieve a desired effect in modulation or treatment of an undesired existing condition in a living being, such as a medical, agricultural or or cosmetic effect. Thus, biologically active substances are generally selected from the broad categories of medicaments, radioisotopes, agricultural products and cosmetics. Representative biologically active substances are disclosed in Table 1 below.

Briefly, the preferred method of the invention for making MVL is as follows. The first step is making a "water-in-oil" emulsion by dissolving amphipathic lipids containing at least one neutral lipid in one or more volatile organic solvents for the lipid component, adding to the lipid component an immiscible first aqueous component and a biologically active substance to be encapsulated, and adding to either or both the lipid component and the first aqueous component, a non-hydrohalic acid effective in modulating the release rate of the encapsulated biologically active substances from the MVL. The mixture is then emulsified, and then mixed with a second immiscible aqueous component to form a second emulsion. The emulsions are formed either mechanically, by ultrasonic energy, nozzle atomization, and the like, or by combinations thereof, to form solvent spherules suspended in the second aqueous component. The solvent spherules contain multiple aqueous droplets with the substance to be encapsulated dissolved in them.

The organic solvent is removed from the spherules, generally by evaporation, for instance, by reduced pressure or by passing a stream of gas over or through the suspension. When the solvent is completely removed, the spherules become MVL. Representative gases satisfactory for use in evaporating the solvent include nitrogen, helium, argon, oxygen, hydrogen, carbon dioxide, or combinations thereof.

The non-hydrohalic acid present when the MVL is formed is effective in controlling the rate of release of the encapsulated biologically active substance from the MVL into biological fluids and in vivo. The acids include, but are not limited to, perchloric acid, nitric acid, glucuronic acid, citric acid, formic acid, acetic acid, trifluoroacetic acid, trichloroacetic acid, sulfuric acid, phosphoric acid, and combinations thereof. The amount of the acid used is that effective to provide a desired and controlled rate of release, which results in therapeutic levels of the encapsulated biologically active substance being released into a biological fluid or in vivo. For example, the concentration of the non-hydrohalic acid in the lipid component or the first aqueous component to which it is added may be in the range of 0.1 mM to about 0.5 M and preferably from about 10 mM to about 200 mM.

Many different types of volatile hydrophobic solvents such as ethers, hydrocarbons, halogenated hydrocarbons, or Freons may be used as the solvent in the lipid component. For example, diethyl ether, isopropyl and other ethers, chloroform, tetrahydrofuran, halogenated ethers, esters, and combinations thereof are satisfactory.

Various types of lipids can be used to make the multivesicular liposomes, and the only requirements regarding lipids for making multivesicular liposomes are that at least one amphipathic lipid and one neutral lipid be included in the lipid component. The amphipathic lipids can be zwitterionic, acidic or cationic lipids. Examples of zwitterionic amphipathic lipids are phosphatidylcholines, phosphatidylethanolamines, sphingomyelins etc. Examples of acidic amphipathic lipids are phosphatidylglycerols, phosphatidylserines, phosphatidylinositols, phosphatidic acids, etc. Examples of cationic amphipathic lipids are diacyl trimethylammonium propanes, diacyl dimethylammonium propanes, stearylamine etc. Examples of neutral lipids include diglycerides, such as diolein, dipalmitolein, and mixed caprylin-caprin; triglycerides, such as triolein, tripalmitolein, trilinolein, tricaprylin, and trilaurin; and combinations thereof Additionally, cholesterol or plant sterols can be used to make multivesicular liposomes.

Many and varied biological substances and therapeutic agents can be incorporated by encapsulation within the MVL. The drugs that can be incorporated into the dispersion system as therapeutic agents include chemicals as well as biologics. The term "chemicals" encompasses compounds that are classically referred to as drugs, such as antitumor agents, anaesthetics, analgesics, antimicrobial agents, opiates, hormones etc. Of particular interest are amikacin, morphine, hydromorphone, cytarabine, methotrexate, 5-fluorouracil (5-FU), floxuridine (FUDR), bleomycin, 6-mercapto-purine, 6-thioguanine, fludarabine phosphate, vincristine, and vinblastine.

The term "biologics" encompasses nucleic acids (DNA and RNA), proteins and peptides, and includes compounds such as cytokines, hormones (pituitary and hypophyseal hormones), growth factors, vaccines etc. Of particular interest are interleukin-2, insulin-like growth factor-1, interferons, insulin, heparin, leuprolide, granulocyte colony stimulating factor (G-CSF), granulocyte-macrophage colony stimulating factor (GM-CSF), tumor necrosis factor, inhibin, tumor growth factor alpha and beta, Mullerian inhibitory substance, calcitonin, and hepatitis B vaccine.

The following TABLE 1 includes a list of classes of biologically active substances effective in humans that can be encapsulated in MVL in the presence of a release-rate modifying non-hydrohalic acid of the invention, and also includes biologically active substances effective for agricultural uses.

TABLE 1

| Antianginas | Antiarrhythmics | Antiasthmatic Agents |
|---|---|---|
| Antibiotics | Antidiabetics | Antifungals |
| Antihistamines | Antihypertensives | Antiparasitics |
| Antineoplastics | Antivirals | Cardiac Glycosides |
| Herbicides | Hormones | Immunomodulators |
| Monoclonal Antibodies | Neurotransmitters | Nucleic Acids |
| Pesticides | Proteins | Radio Contrasts |
| Radionuclides | Sedatives and Analgesics | Steroids |
| Tranquilizers | Vaccines | Vasopressors |
| Anesthetics | Peptides | |

The term "therapeutically effective" as it pertains to the compositions of the invention means that a biologically active substance present in the first aqueous component within the vesicles is released in a manner sufficient to achieve a particular medical effect for which the therapeutic agent is intended. Examples, without limitation, of desirable medical effects that can be attained are chemotherapy, antibiotic therapy, and regulation of metabolism. Exact dosages will vary depending upon such factors as the particular therapeutic agent and desirable medical effect, as well as patient factors such as age, sex, general condition, and the like. Those of skill in the art can readily take these factors into account and use them to establish effective therapeutic concentrations without resort to undue experimentation.

Generally, however, the dosage range appropriate for human use includes the range of 0.1–6000 mg/sq m of body surface area. For some applications, such as subcutaneous administration, the dose required may be quite small, but for other applications, such as intraperitoneal administration, the dose desired to be used may be very large. While doses outside the foregoing dose range may be given, this range encompasses the breadth of use for practically all the biologically active substances.

The MVL may be administered for therapeutic applications by any desired route, for example, intramuscular, intraarticular, epidural, intrathecal, intraperitoneal, subcutaneous, intravenous, intralymphatic, oral and submucosal, and by implantation under many different kinds of epithelia, including the bronchialar epithelia, the gastrointestinal epithelia, the urogenital epithelia, and various mucous membranes of the body.

In addition, the MVL of the invention can be used to encapsulate compounds useful in agricultural applications, such as fertilizers, pesticides, and the like. For use in agriculture, the MVL can be sprayed or spread onto an area of soil where plants will grow and the agriculturally effective compound contained in the vesicles will be released at a controlled rate by contact with rain and irrigation waters. Alternatively the slow-releasing vesicles can be mixed into irrigation waters to be applied to plants and crops. One skilled in the art will be able to select an effective amount of the compound useful in agricultural applications to accomplish the particular goal desired, such as the killing of pests, the nurture of plants, etc.

The following examples illustrate the manner in which the invention can be practiced. It is understood, however, that the examples are for the purpose of illustration and the invention is not to be regarded as limited to any of the specific materials or conditions therein.

EXAMPLE 1

This example demonstrates that the release rate of a biologically active substance into an in vitro medium can be controlled by the use of different acids.

Step 1) In a clean glass cylinder (2.5 cm inner diameter× 10.0 cm height), 5 mL of a solution containing 46.5 $\mu$moles of 1,2-dioleoyl-sn-glycero-3-phosphocholine, 10.5 $\mu$moles of 1,2-dipalmitoyl-sn-glycero-3-phosphoglycerol, 75 $\mu$moles of cholesterol, 9.0 $\mu$moles of triolein in chloroform were placed (the lipid component. The lipids were purchased from Avanti Chemical Company (Alabaster, Ala.).

Step 2) Five mL of the first aqueous component, and cytarabine (20 mg/mL) dissolved in 0.136 M of one of the acids to be tested was added into the above glass cylinder containing the lipid component. The acids tested as a release-rate modifying agent were: perchloric, nitric, formic, sulfuric, phosphoric, acetic, trichloroacetic, and trifluoroacetic acids.

Step 3) For making the water-in-oil emulsion, a homogenizer (AutoHomoMixer, Model M, Tokushu Kika, Osaka, Japan) was used by mixing for 8 minutes at a speed of 9000 rpm.

Step 4) For making the chloroform spherules suspended in water, 20 mL of a solution containing 4 wt % glucose and 40 mM lysine was layered on top of the water-in-oil emulsion, and then mixed for 60 seconds at a speed of 4000 rpm to form the chloroform spherules.

Step 5) The chloroform spherule suspension in the glass cylinder was poured into the bottom of a 1000 mL Erlenmeyer flask containing 30 mL of water, glucose (3.5 g/100 mL), and free-base lysine (40 mM). A stream of nitrogen gas was passed at a flow-rate of 7 L/minute over the suspension in the flask to evaporate chloroform over 20 minutes at 37° C. Sixty mL of normal saline (0.9% sodium chloride) was added to the flask. The MVL were then isolated by centrifugation at 600 X g for 10 minutes. The supernatant was decanted, and the pellet was resuspended in 50 mL of normal saline. The pellet was resuspended in saline to yield a final concentration of 10 mg cytarabine per mL of suspension.

A laser diffraction particle size analyzer (Horiba Instruments, Irvine, Calif.) was used to determine particle size. The average length-weighted mean diameter of the resulting MVL particles was in the range from 12–16 $\mu$m.

The use of different non-hydrohalic acids as release-modifying agents had marked influence on the rate of cytarabine release from the MVL incubated in human plasma. The percent of cytarabine retained in the MVL after incubation at 37° C. in human plasma for the different acids is measured as a function of time of incubation. The half-life of drug release, calculated assuming a single-exponential, is given in TABLE 2. The data in TABLE 2 are the mean and standard deviation from three experiments.

TABLE 2

| Acid | Half Life in Days for Release of Cytarabine |
| --- | --- |
| Perchloric Acid | 37.2 ± 8.0 |
| Nitric Acid | 54.5 ± 5.7 |
| Phosphoric Acid | 6.5 ± 0.2 |
| Formic Acid | 5.6 ± 0.2 |
| Trichloroacetic Acid | 5.5 ± 0.6 |
| Acetic Acid | 4.8 ± 0.5 |
| Trifluoroacetic Acid | 3.4 ± 0.4 |
| Sulfuric Acid | 1.6 ± 0.5 |

The nature of the release-rate modifying non-hydrohalic acid used to prepare the multivesicular liposomes had a profound effect on the release rates of cytarabine in human plasma. Use of monoprotic inorganic acids, namely, nitric acid, and perchloric acid, resulted in the slowest release rate for cytarabine. Diprotic and triprotic acids, i.e., sulfuric acid and phosphoric acid, resulted in fast release rates. The organic acids, formic acid, acetic acid, trifluoroacetic acid and trichloroacetic acid, also resulted in fast release rates. Thus, a desired release rate can be achieved by selecting an appropriate acid as illustrated herein.

EXAMPLE 2

This example demonstrates that the rate of release of leuprolide from MVL into an in vitro medium can be controlled by varying the acid.

Step 1) In a clean conical Teflon tube, 2 mL of a solution containing 78.88 $\mu$moles of 1,2-dioleoyl-sn-glycero-3-phosphocholine, 16.65 $\mu$moles of 1,2-dipalmitoyl-sn-glycero-3-phosphoglycerol, 118.8 $\mu$moles of cholesterol, 14.6 $\mu$moles of triolein in chloroform were placed (the lipid component). The lipids were purchased from Avanti Chemical Company (Alabaster, Ala.).

Step 2) Two mL of first aqueous component, leuprolide (10 mg/nL) dissolved 0.1 M phosphoric acid, or ascorbic acid, or 0.2 M citric acid, or glucuronic acid, were added into the above Teflon tube containing lipid component.

Step 3) For making the water-in-oil emulsion, a homogenizer (AutoHomoMixer, Model M, Tokushu Kika, Osaka, Japan) was used by mixing for 7 minutes at a speed of 10,000 rpm.

Step 4) For making the chloroform spherules suspended in water, 20 mL of a solution containing 4 wt % glucose and 40 mM lysine was added to the water-in-oil emulsion, and then mixed for 2 minutes at a speed of 2000 rpm to form the chloroform spherules.

Step 5) The chloroform spherule suspension in the glass cylinder was poured into the bottom of a 1000 mL Erlenmeyer flask containing 30 mL of water, 4 wt % glucose, and 40 mM free-base lysine. A stream of nitrogen gas was passed at a flow-rate of 50 cu ft/hr over the suspension in the flask to evaporate chloroform over 20 minutes at 37° C. The MVL were then isolated by centrifugation at 600 X g for 10 minutes.

The half life values in days for the plasma release were 15.8±8.4, 4.7±1.5, 6.0±1.5, and 3.0±0.2, for phosphoric acid, ascorbic acid, citric acid, and glucuronic acid, respectively.

EXAMPLE 3

This example demonstrates that a mixture of zwitterionic amphipathic lipids and a neutral lipid can be used for producing the MVL compositions with an acid used in the process.

The procedure for the preparation of MVL was the same as in EXAMPLE 1, with the following exceptions.

For Step 1, into a clean glass cylinder (2.5 cm inner diameter×10.0 cm height) were placed 5 mL of a solution containing 13.20 $\mu$moles of 1,2-dioleoyl-sn-glycero-3-phosphocholine, 2.79 $\mu$moles of 1,2-dipalmitoyl-sn-glycerol-3-phosphoethanolamine, 19.88 $\mu$moles of cholesterol, and 2.48 $\mu$moles of triolein in chloroform (the lipid component).

In Step 2, 5 mL of the first aqueous component and cytarabine (20 mg/mL) dissolved in 0.136 M sulfuric acid were added into the above glass cylinder containing the lipid component.

The half life value for in vitro release was 3.0±1.6 days.

EXAMPLE 4

This is an example for the antibacterial agent, amikacin, encapsulated into MVL in the presence of an non-hydrohalic acid.

The procedure for the preparation of MVL was the same as in EXAMPLE 1, with the following exceptions.

For Step 1, into a clean glass cylinder (2.5 cm inner diameter×10.0 cm height) were placed 5 mL of a solution containing 13.20 $\mu$moles of 1,2-dioleoyl-sn-glycero-3-phosphocholine, 2.79 $\mu$moles of 1,2-dipalmitoyl-sn-glycero-3-phosphoglycerol, 19.88 $\mu$moles of cholesterol, 2.48 $\mu$moles of triolein in chloroform (the lipid component).

In Step 2, 5 mL of the first aqueous component and amikacin (20 mg/mL) dissolved in 0.136 M sulfuric acid were added into the above glass cylinder containing the lipid component.

The half life value in plasma was 16.6±2.1 days.

Thus, the present disclosure provides "depot" preparations of wide application and uses in which biologically active substances are encapsulated in relatively large amounts, provide sustained exposure or delivery at therapeutic concentrations of these substances for optimal results, and the release rate of the substance is controlled by varying the nature of the acid used in the formulation.

For a given biologically active substance, one skilled in the art will be able to choose an acid to produce an MVL composition with a desired release rate of the encapsulated biologically active substance.

The present invention, therefore, is well suited and adapted to attain the ends and objects and has the advantages and features mentioned as well as others inherent therein.

While presently preferred embodiments of the invention have been given for the purpose of disclosure, it should be understood that various modifications can be made without departing from the spirit and scope of the invention. Accordingly, the following claims are intended to be interpreted to embrace all such modifications.

What is claimed is:

1. A multivesicular liposome having multiple non-concentric chambers with internal membranes distributed as a network throughout, produced by a method comprising the steps of:
   (a) forming a water-in-oil emulsion from two immiscible components, the two immiscible components being:
      1) a lipid component comprising at least one organic solvent, at least one amphipathic lipid, and at least one neutral lipid lacking a hydrophilic head group, and
      2) a first aqueous component;
   said water-in-oil emulsion further comprising:
      3) non-hydrohalic acid in a concentration range from about 0.1 mM to about 0.5 M, wherein the concentration is selected to provide controlled release of the biologically active substance in 4) from the liposome, and
      4) at least one biologically active substance;
   said non-hydrohalic acid and said biologically active substance being independently incorporated into the lipid component, the first aqueous component, or both;
   (b) mixing the water-in-oil emulsion containing the non-hydrohalic acid with a second aqueous component to form solvent spherules; and thereafter
   (c) removing the organic solvent from the solvent spherules to form multivesicular liposomes.

2. The liposome of claim 1, wherein the acid is selected from the group consisting of sulfuric acid, phosphoric acid, and acetic acid, and combinations thereof and wherein the controlled release is at physiologic conditions.

3. The liposome of claim 1, wherein the acid is selected from the group consisting of nitric, formic, sulfuric, phosphoric, acetic, glucuronic, citric, and combinations thereof.

4. The liposome of claim 1, wherein the biologically active agent is selected from the group consisting of an antitumor agent, an anaesthetic, an analgesic, an antimicrobial agent, a hormone, an antiasthmatic agent, a cardiac glycoside, an antihypertensive, a vaccine, an antiarrhythmic, an immunomodulator, a steroid, a monoclonal antibody, a neurotransmitter, a radionuclide, a radio contrast agent, a nucleic acid, a protein, a herbicide, a pesticide, and suitable combinations thereof.

5. The liposome of claim 1, wherein the biologically active substance is cytarabine.

6. The liposome of claim 1, wherein the biologically active substance is amikacin.

7. The liposome of claim 1, wherein the biologically active substance is hydromorphone.

8. The liposome of claim 1, wherein the biologically active substance is leuprolide.

9. The liposome of claim 1, wherein the biologically active substance is insulin.

10. The liposome of claim 1, wherein the biologically active substance is interleukin-2.

11. The liposome of claim 1, wherein the biologically active substance is insulin-like growth factor-1.

12. The liposome of claim 1, wherein the biologically active substance is an interferon.

13. The liposome of claim 1, wherein the biologically active substance is granulocyte colony stimulating factor (G-CSF).

14. The liposome of claim 1, wherein the biologically active substance is tumor necrosis factor.

15. The liposome of claim 1, wherein the biologically active substance is tumor growth factor alpha.

16. The liposome of claim 1, wherein the biologically active substance is tumor growth factor beta.

17. The liposome of claim 1, wherein the biologically active substance is morphine.

18. The liposome of claim 1, wherein the controlled release of the biologically active substance is sufficient to ameliorate a disease following administration of the liposome to a living mammal.

19. The liposome of claim 1, wherein the biologically active substance is selected from the group consisting of herbicides and pesticides.

20. The liposome of claim 1, wherein the amphipathic lipid is provided in admixture with cholesterol, plant sterols, or combinations thereof.

21. The liposome of claim 1, wherein the amphipathic lipid is a zwitterionic lipid.

22. The liposome of claim 1, wherein the amphipathic lipid is an anionic lipid.

23. The liposome of claim 1, wherein the amphipathic lipid is a mixture of a zwitterionic lipid and an anionic lipid.

24. The liposome of claim 1, wherein the amphipathic lipid is a mixture of a zwitterionic lipid and a cationic lipid.

25. The liposome of claims 1, 20, 22, and 23, wherein the zwitterionic lipid is selected from the group consisting of phosphatidylcholines, phosphatidylethanolamines, sphingomyelins, lysophosphatidylcholines, lysophosphatidylethanolamines, and combinations thereof.

26. The liposome of claims 1, 21, and 22, wherein the anionic lipid is selected from the group consisting of phosphatidylglycerols, phosphatidylserines, phosphatidylinositols, phosphatidicacids, cardiolipins, and combinations thereof.

27. The liposome of claims 1 and 23, wherein the cationic lipid is selected from the group consisting of diacyl trimethylammonium propanes, diacyl dimethylammonium propanes, stearylamine, and combinations thereof.

28. The liposome of claim 1, wherein the neutral lipid is selected from the group consisting of triglycerides, diglycerides, ethylene glycols, and combinations thereof.

29. The liposome of claim 1, wherein the organic solvent is selected from the group consisting of ethers, hydrocarbons, halogenated hydrocarbons, halogenated ethers, esters, and combinations thereof.

30. The liposome of claim 1, wherein the emulsification of the two immiscible components is carried out using a method selected from the group consisting of mechanical agitation, ultrasonic energy agitation, and nozzle atomization.

31. The liposome of claim 1, wherein the formation of the solvent spherules is carried out using a method selected from the group consisting of mechanical agitation, ultrasonic energy agitation, and nozzle atomization.

32. The liposome of claim 1, wherein the removal of the organic solvent is by a method selected from the group consisting of sparging, rotary evaporation, passing gas over the solvent spherule suspension, solvent selective filtration, and combinations thereof.

33. The liposome of claim 1, wherein the concentration of the organic solvent is in the range from about 3.98 mM to about 15 mM, the concentration of the amphipathic lipid is in the range from about 3.2 mM to about 47.77 mM, and the concentration of the neutral lipid is in the range from about 0.5 mM to about 7.3 mM.

34. The liposome of claim 33, wherein the amphipathic lipid is a combination of 1,2-dioleoyl-sn-glycero-3-phosphocholine (DOPC) in a concentration from about 2.64 mM to about 39.44 mM and 1,2-dipalmitoyl-sn-glycero-3-phosphoglycerol (DPPG) in a concentration from about 0.56 to about 8.33 mM.

35. The liposome of claim 1, wherein the non-hydrohalic acid is selected from the group consisting of nitric acid, glucuronic acid, citric acid, formic acid, acetic acid, sulfuric acid, phosphoric acid, and combinations thereof.

* * * * *

UNITED STATES PATENT AND TRADEMARK OFFICE
CERTIFICATE OF CORRECTION

PATENT NO. : 6,132,766
DATED : OCTOBER 17, 2000
INVENTOR(S) : SANKARAM BHIMA MANTRIPRAGADA, PH.D. ET AL.

It is certified that error appears in the above-identified patent and that said Letters Patent is hereby corrected as shown below:

Page 2, Col. 2: Kim, [Kim, Kim,] Cancer Chemother. Pharmacol., 33:187-190, 1993, "Extended-release formulation of morphine for subcutaneous administration".

Col. 5, Lines 57-58 (Table 1) reformatted:

TABLE 1

| | | |
|---|---|---|
| Antianginas | Antiarrhythmics | Antiasthmatic Agents |
| Antibiotics | Antidiabetics | Antifungals |
| Antihistamines | Antihypertensives | Antiparasitics |
| Antineoplastics | Antivirals | Cardiac Glycosides |
| Herbicides | Hormones | Immunomodulators |
| Monoclonal Antibodies | Neurotransmitters | Nucleic Acids |
| Pesticides | Proteins | Radio Contrasts |
| Radionuclides | Sedatives and Analgesics | Steroids |
| Tranquilizers | Vaccines | Vasopressors |
| Anesthetics | Peptides | |

UNITED STATES PATENT AND TRADEMARK OFFICE
CERTIFICATE OF CORRECTION

PATENT NO. : 6,132,766
DATED : OCTOBER 17, 2000
INVENTOR(S) : SANKARAM BHIMA MANTRIPRAGADA, PH.D. ET AL.

It is certified that error appears in the above-identified patent and that said Letters Patent is hereby corrected as shown below:

Col. 6, Line 55: (the lipid component).

Col. 7, Line 67: "10 mg/[nL]mL

Signed and Sealed this

Fifteenth Day of May, 2001

Attest:

NICHOLAS P. GODICI

Attesting Officer     Acting Director of the United States Patent and Trademark Office